United States Patent [19]

Schleppnik

[11] 4,310,512
[45] Jan. 12, 1982

[54] DERIVATIVES OF ACETIC AND PROPIONIC ACIDS, COMPOSITIONS CONTAINING SAME AND USE AS MALODOR COUNTERACTANTS

[75] Inventor: Alfred A. Schleppnik, St. Louis, Mo.

[73] Assignee: Bush Boake Allen Inc., Norwood, N.J.

[21] Appl. No.: 99,993

[22] Filed: Dec. 4, 1979

Related U.S. Application Data

[63] Continuation of Ser. No. 828,374, Aug. 29, 1977, abandoned.

[51] Int. Cl.³ ............................................. A61L 13/00
[52] U.S. Cl. .................................. 424/76; 252/522 A; 252/522 R; 424/45; 424/307; 424/308; 560/17; 560/61; 560/138; 560/140
[58] Field of Search ........................... 424/45, 76, 308; 252/522

[56] References Cited

U.S. PATENT DOCUMENTS

| | | | |
|---|---|---|---|
| 2,170,995 | 8/1939 | Grether | 560/61 |
| 2,863,907 | 12/1958 | Schmerling | 260/473 |
| 3,494,957 | 2/1970 | Nakanishi et al. | 260/473 |
| 4,046,802 | 9/1977 | Elliott et al. | 560/61 |

FOREIGN PATENT DOCUMENTS 2130063  12/1972  Fed. Rep. of Germany .

*Primary Examiner*—Allen J. Robinson
*Attorney, Agent, or Firm*—Frishauf, Holtz, Goodman & Woodward

[57] ABSTRACT

Compounds of the formula

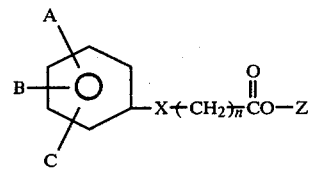

wherein
A, B, C individually represent hydrogen or an alkyl group of 1 to 6 carbon atoms, provided that the total combined number of carbon atoms of A, B and C does not exceed 8;
X represents oxygen, sulfur,

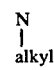

wherein the alkyl group has 1 to 7 carbon atoms or

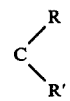

wherein R and R' represent hydrogen or a methyl group;
n represents 1 or 2; and
Z represents a hydroxyalkyl group of 2 to 7 carbon atoms have been found to be useful in compositions and methods for counteracting malodors.

29 Claims, No Drawings

DERIVATIVES OF ACETIC AND PROPIONIC ACIDS, COMPOSITIONS CONTAINING SAME AND USE AS MALODOR COUNTERACTANTS

CROSS-REFERENCES TO RELATED APPLICATIONS

This is a continuation of application Ser. No. 828,374, filed Aug. 29, 1977, now abandoned.

FIELD OF THE INVENTION

This invention relates to the art of the treatment of offensive odors. More particularly, the invention relates to compounds, compositions and methods found effective to counteract malodors.

BACKGROUND OF THE INVENTION

The art of perfumery began, perhaps, in the ancient cave dwellings of prehistoric man. From its inception, and until comparatively recently, the perfumer has utilized natural perfume chemicals of animal and vegetable origin. Thus, natural perfume chemicals such as the essential oils, for example, oil of rose and oil of cloves, and animal secretions such as musk, have been manipulated by the perfumer to achieve a variety of fragrances. In more recent years, however, research perfume chemists have developed a large number of synthetic odoriferous chemicals possessing aroma characteristics particularly desired in the art. These synthetic aroma chemicals have added a new dimension to the ancient art of the perfumer, since the compounds prepared are usually of a stable chemical nature, are inexpensive as compared with the natural perfume chemicals and lend themselves more easily to manipulation than the natural perfume chemicals since such natural perfume chemicals are usually a complex mixture of substances which defy chemical analysis. In contrast thereto, the synthetic aroma chemicals possess a known chemical structure and may therefore be manipulated by the perfumer to suit specific needs. Such needs vary over a very wide spectrum. Accordingly, there is a great need in the art of fragrance compositions for compounds possessing specific olfactory characteristics.

Heretofore a major effort in the art of perfumery has been directed to providing means of treating odors that are offensive to the human sense of smell. Such odors encompass a variety of odors such as bathroom-odor, kitchen-odor, body-odor, cigar smoke-odor, etc. Many products have been developed in an attempt to overcome these odors. So-called "room fresheners" or "deodorants" are illustrative of such products.

In general these products provide a masking effect by one of two mechanisms. The maskant fragrance is provided either to suppress the offensive odor by providing a more pleasing aroma in large quantities or by providing an aroma that blends with the offensive odor to provide a different and more desirable aroma. Unfortunately, in both instances a large amount of fragrance must be utilized which in itself often proves to be offensive. Furthermore, the offensive odor is usually still detectable at the levels of maskant fragrances that are reasonably tolerable. Accordingly, compositions and methods for counteracting such offensive odors which would substantially eliminate such odors without the above-noted disadvantages are particularly desirable.

Particularly noxious odors are caused by compounds which have a pronounced tendency to either donate or accept protons. Such compounds will hereinafter be referred to as "malodors". They include the notorious olfactory classes of lower carboxylic acids, thiols, thiophenols, phenols, lower amines, phosphines and arsines.

DESCRIPTION OF THE PRIOR ART

U.S. Pat. No. 2,170,995 discloses certain ethylene glycol aryloxyacetates which are disclosed to be useful as plasticizers.

SUMMARY OF THE INVENTION

The present invention provides novel compounds and compositions which are especially useful in view of their ability to counteract malodors. Furthermore, novel methods are provided, i.e. the use of such novel compounds and compositions to counteract malodors.

The present invention provides compounds of the formula

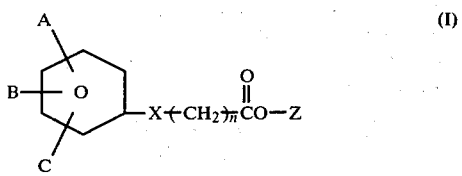

wherein

A, B, C individually represent hydrogen or an alkyl group of 1 to 6 carbon atoms, provided that the total combined number of carbon atoms of A, B and C does not exceed 8;

X represents oxygen, sulfur,

wherein the alkyl group has 1 to 7 carbon atoms or

wherein R and R' represent hydrogen or a methyl group;

n represents 1 or 2; and

Z represents an alkyl group of 2 to 7 carbon atoms, said alkyl group containing at least one hydroxyl group which are useful in formulating compositions for counteracting malodors.

Within the scope of Formula (I), the present invention provides novel compounds characterized by the formula

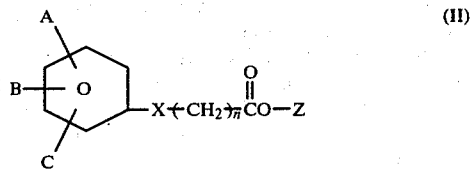

wherein

A, B, C individually represent hydrogen or an alkyl group of 1 to 6 carbon atoms, provided that the total number of carbon atoms of A, B and C does not exceed 8;

X represents oxygen, sulfur or

|
alkyl wherein the alkyl group has 1 to 7 carbon atoms;
n represents 1 or 2; and
Z represents an alkyl group of 4 to 7 carbon atoms when X represents O or S and Z represents an alkyl group of 2 to 7 carbon atoms when X represents

|
alkyl said alkyl group represented by Z containing at least one hydroxyl group.

In addition to the compounds described above, the present invention contemplates derivatives wherein Z represents alkyl rather than hydroxyalkyl and wherein such alkyl may cyclize with alkyl substituents on the benzene ring.

DESCRIPTION OF THE PREFERRED EMBODIMENTS

The term "counteract" as used herein means the effect on the human sense or smell and/or the malodor resulting in alleviating the offensiveness of the malodor to the human sense of smell. It is not intended that this term be limited to any particular mechanism by which such a result may be obtained.

Surprisingly, the compounds of the present invention are capable of effectively counteracting malodors when utilized in small quantities. The compounds of the present invention can be used in many different mediums to counteract malodors. For instance, use in room fresheners or deodorants in the form of aerosols (sprays, etc.), liquids (wick type), solids (wax bases as in pomander, plastics, etc.), powders (sachets, dry sprays) and gels (solid gel sticks) are particularly preferred. Other illustrative uses are in clothes deodorants as applied by washing machine applications such as in detergents, powders, liquids, whiteners or fabric softeners or by other applications such as closet blocks, closet aerosol sprays, or clothes storage areas or in dry cleaning to overcome residual solvent notes on clothes; in cleansers such as disinfectants and toilet bowl cleaners; in bathroom accessories such as paper towels, bathroom tissues, sanitary napkins, towellets, disposable wash cloths, disposable diapers, and diaper pail deodorants; in cosmetic products such as antiperspirant and underarm deodorants, general body deodorants in the form of powders, aerosols, liquids or solid, or hair care products such as hair sprays, conditioners, rinses, hair colors and dyes, permanent waves, depilatories, hair straighteners, hair groom applications such as pomades, creams, lotions, etc., medicated hair care products containing such ingredients as S-selenium-sulfide, coal tar, salicylates, etc., or shampoos, or foot care products such as foot powders, liquids, or colognes, aftershaves and body lotions, or soaps and synthetic detergents such as bars, liquids, foams, or powders; in odor control such as during manufacturing processes, such as in the textile finishing industry and the printing industry (inks and paper); in effluent control such as in processes involved in pulping, stock yard and meat processing, sewage treatment, or garbage disposal, or in product control as in textile finished goods, rubber finished goods, car fresheners, etc.; in agricultural and pet care products such as dog and hen house effluents, and domestic animal and pet care products such as deodorants, shampoo or cleaning agents, or animal litter materials; in large scale closed air systems such as auditoriums, and subways and transport systems.

The amount of the compounds of the present invention to be utilized depends, in general, on the particular malodor involved and its concentration and on other variables such as the medium in which it is used and the temperature, humidity and air circulation. An effective amount should be used. In general, the compounds of the present invention are effective when present in the air (in which the malodor is located) at a level as low as about 0.01 mg./cubic meter of air. Any concentration above this amount will generally be effective. However, from a practical point of view, more than about 1 mg./cubic meter of air is probably unnecessary with even the most offensive and concentrated malodors.

The compounds of the present invention are prepared in a known manner by reacting, where X represents

oxygen or sulfur, the appropriate aryloxy- or arylmercapto- acetic, propionic acid or butyric acid (i.e. where X represents $CH_2$ and $n=2$) having the formula

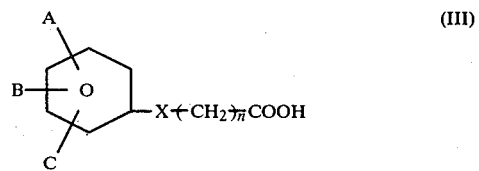

(III)

wherein A, B, C, X and n have been defined above in Formula (I), with an appropriate polyol, preferably a glycol, or its corresponding alkylene oxide.

Where X represents

|
alkyl the compounds of the present invention are prepared by the reaction of an ester of N-alkyl-N-phenylglycine with an appropriate polyol, preferably a glycol.

Alkyl N-alkyl N-phenylglycinates may be prepared, by way of example, by reaction of an N-alkyl N-phenylglycine with an alkyl chloroacetate.

As specifically illustrated in the following examples, reaction of the appropriate aryloxy- or arylmercaptoacid with the appropriate polyol was conducted in an inert diluent, e.g. benzene, toluene, cyclohexane or xylene, in the presence of an acid catalyst such as hydrochloric acid, a strong acid ion-exchange resin or toluene sulfonic acid at elevated temperatures, preferably at the reflux temperature of the mixture. The product is obtained by crystallization or distillation.

Reaction of the appropriate aryloxy- or arylmercapto- acid and an alkylene oxide was conducted in water in the presence of a base such as sodium hydroxide or potassium hydroxide at a temperature of from about 0°–50° C. Following extraction into an organic solvent, washing to remove unreacted organic acid, drying and removal of the solvent the product is obtained by crystallization or distillation.

Reaction of esters of N-alkyl N-phenylglycine with an appropriate polyol was conducted without solvent by heating the reactants to approximately 150° C. in the presence of an alkoxide base such as sodium methoxide or potassium ethoxide. After acidification and removal of unreacted polyol by distillation, the product was obtained by crystallization or fractional distillation.

Exemplary compounds of Formula (III) which are used to prepare the compounds of the invention include phenoxyacetic acid, p-isopropylphenoxyacetic acid, o-methylphenoxyacetic acid, p-tert-butylphenoxyacetic acid, 3,4-dimethylphenoxyacetic acid, 5,6,7,8-tetrahydronaphthoxyacetic acid, phenylmercaptoacetic acid, 3-phenoxypropionic acid, 3-phenylpropionic acid (i.e. where $X=CH_2$ and $n=1$), 2-phenoxypropionic acid and 4-phenylbutyric acid (i.e. where $X=CH_2$ and $n=2$).

Exemplary polyols which are utilized to prepare the compounds of the invention include ethylene glycol, butylene glycol, 1,2-propanediol, 1,3-propanediol, 1,3-butanediol, 1,4-butanediol and 1,6-hexanediol.

Exemplary alkylene oxides include ethylene oxide and 1,2-propylene oxide.

Exemplary N-alkyl N-phenylglycinates which are used to prepare the compounds of the invention include methyl N-methyl N-phenylglycinate, ethyl N-butyl-N-phenyl glycinate and propyl N-heptyl-N-phenylglycinate.

The following examples illustrate the method of preparing representative compounds of the present invention.

EXAMPLE 1

Preparation of Mono Ethylene Glycol Phenoxy Acetate

Into a 5000 ml. 3-necked flask, equipped with thermometer, stirrer, condenser and Dean-Stark trap were weighed 924 gms. of phenoxyacetic acid. There were added 2 gms. toluene sulfonic acid as catalyst and 100 mls. of benzene. Heating was started with stirring and there were added 2270 gms. of ethylene glycol. At reflux temperature water was collected and taken off. After 11 and ½ hours of refluxing the reaction mixture was transferred to a 6 liter separatory funnel where excess ethylene glycol was separated and recovered. The benzene layer was extracted with hot water and sodium bicarbonate and the benzene layer was filtered warm through a molecular sieve to remove residual water. The benzene extract was allowed to stand overnight and the crystals which formed were removed by filtration and dried in a vacuum oven. A total of 370.2 gms. product was recovered, m.p. 61°–63° C.

In the same manner the compounds set forth in Table 1, below were prepared, except that some products were obtained by distillation instead of crystallization.

TABLE 1

| Example | Acid | Polyol | Product |
|---|---|---|---|
| 2 | p-tert-butyl phenoxyacetic | ethylene glycol | Mono ethylene glycol p-tert-butyl phenoxyacetate, m.p. 70–72° C. |
| 3 | phenoxyacetic | 1,6-hexanediol | 6-hydroxyhexyl phenoxyacetate, b.p. (0.13 mm.) 153–170° C. |
| 4 | phenoxyacetic | 1,4-butanediol | 4-hydroxybutyl phenoxyacetate, b.p. (0.09 mm.) 148–155° C. |
| 5 | 2-methyl phenoxyacetic | butylene glycol | 3-hydroxypropyl-2'-methyl phenoxyacetate, b.p. (0.28 mm.) 139–150° C. |
| 6 | phenoxyacetic | 1,3-butanediol | 3-hydroxy-1-butyl phenoxyacetate and 1-hydroxy-3-butyl phenoxyacetate as mixture of 2 parts "1" ester to 1 part "3" ester, b.p. (0.30 mm.) 139–141° C. |
| 7 | 3-phenoxypropionic | ethylene glycol | 2'-hydroxyethyl 3-phenoxypropionate, m.p. 64.5–66.5° C. |
| 8 | phenoxyacetic | 1,2-propanediol | 2-hydroxy-1-propyl phenoxyacetate and 1-hydroxy-2-propyl phenoxyacetate as approximately 1:1 mixture, b.p. (0.20 mm.) 132–135° C. |
| 9 | phenylmercaptoacetic | ethylene glycol | 2'-hydroxyethyl phenylmercaptoacetate, b.p. (0.80 mm.) 156–170° C. |
| 10 | 3-phenylpropionic | ethylene glycol | 2'hydroxyethyl 3-phenylpropionate, b.p. (0.33 mm.) 134.5–148° C. |

EXAMPLE 11

Esterification of p-isopropyl phenoxyacetic acid with Propylene oxide

Into a 500 ml. flask were placed 0.3 gm. sodium hydroxide dissolved in 45 ml. water, 16 gms. p-isopropylphenoxyacetic acid and 53 gms. propylene oxide. This mixture was stirred for 5 days, then extracted with 2×150 ml. ether. The combined organic layers were washed with 100 ml. saturated sodium carbonate solution and with 50 ml. water. After drying with magnesium sulfate and filtering, the material was concentrated on a rotary evaporator. The residual oil was distilled to yield 13.6 gms. product, b.p. (0.18 mm.) 140.5°–156.5° C. Analysis revealed the product to be approximately 70% 2hydroxy-1-propyl p-isopropyl-phenoxyacetate and 30% 1-hydroxy-2-propyl p-isopropylphenoxy-acetate.

EXAMPLES 12 and 13

In the same manner as Example 11, but substituting ethylene oxide and, respectively, 3,4-dimethylphenoxyacetic acid and 5',6',7',8'-tetrahydronaphthoxyacetic acid for p-isopropyl-phenoxyacetic acid, there were obtained the compounds of Table 2, below.

TABLE 2

| Example | Acid | Alkylene oxide | Product |
|---|---|---|---|
| 12 | 3,4-dimethyl | ethylene oxide | 2-Hydroxyethyl 3',4'-dimethylphenoxy- |

TABLE 2-continued

| Example | Acid | Alkylene oxide | Product |
|---------|------|----------------|---------|
| | phenoxyacetic | | acetate, b.p. (0.35 mm.) 147–156° C. Solidifies on cooling, m.p. 55–57° C. |
| 13 | 5',6',7',8'-tetrahydro-naphthoxyacetic | ethylene oxide | 2-Hydroxyethyl 5',6',7',8'-tetrahydro-naphthoxyacetate, b.p. (0.22 mm.) 158–162° C. |

EXAMPLE 14

Preparation of 2-Hydroxyethyl N-methyl-N-phenylglycinate

Into a 100 ml. flask fitted with a condenser and a Dean-Stark trap there were placed 49.5 gms. ethylene glycol, 17 gms. of ethyl N-methyl-N-phenylglycinate and 0.7 gm. sodium methoxide. The flask and contents were heated to 150° C. in an oil bath and stirred for 13 hours. The reaction mixture was allowed to cool to room temperature and 1.25 ml. of concentrated HCl in 3.5 ml. water were added and the mixture was stirred for 10 minutes. After the ethylene glycol was distilled off at atmospheric pressure, 11.5 gms. of product was obtained by vacuum distillation, b.p. (0.3 mm.) 139°–149° C.

EXAMPLE 15

Preparation of p-Isopropylphenoxyacetic Acid

Into a 100 ml. flask there were placed 100 gms. sodium hydroxide in 300 ml. water and the mixture was stirred until all of the sodium hydroxide was dissolved. Without cooling, there were added 60 gms. p-isopropylphenol and 95 gms. chloroacetic acid. The mixture was stirred at a temperature between 95 and 105° C. for 1 hour and then cooled to 40° C. The reaction mixture was adjusted to a pH of approximately 2 by addition of 1 molar HCl, the mixture was cooled to room temperature and extracted with 2×300 ml. ether. Upon treatment of the ether layer with sodium carbonate solution, the sodium salt of the product precipitated. The salt was dissolved in 800 ml. water and acidified with hydrochloric acid to precipitate product. It was filtered, washed with water and dried to afford 25.6 gms. product, m.p. 84.5°–87° C.

The following examples are given to illustrate the malodor counteractant properties of the compounds discussed above. The symbol "mg./cu. meter" refers to the weight (in milligrams) of material present in one cubic meter of air.

EXAMPLE 16

The following malodor concentrate was prepared:

| Bathroom Malodor Concentrate | |
|---|---|
| Component | Parts by Weight |
| skatole | 0.91 |
| β-thionaphthole | 0.91 |
| 95% aqueous solution of thioglycolic acid | 21.18 |
| n-caproic acid | 6.00 |
| p-cresyl isovalerate | 2.18 |
| N-methyl morpholine | 6.00 |

Aerosol cans were prepared of the above malodor with the following concentrations:

| Bathroom Malodor Aerosol | |
|---|---|
| Component | Parts by Weight |
| Bathroom Malodor Concentrate | 0.1 |
| Dipropylene glycol | 4.9 |
| Freon Propellant-F 11/12 (50/50) | 95.0 |

A floral spice fragrance composition was prepared containing 10 percent by weight of the compounds to be tested.

Aerosol cans were prepared of the floral spice fragrance composition with the fragrance composition being present in a concentration of 0.5% with Freon Propellant-F 11/12 (50/50) constituting the remaining material in the system.

Although a floral spice fragrance was used in the present tests, other fragrances may be used, e.g. floral bouquet, cologne spice, lavender bouquet, ozonone type and the like.

A test chamber having inside dimensions of 335 cm×365 cm×243 cm with a total volume of 29.7 cubic meters having an access door and an exhaust fan was provided. The capacity of the exhaust fan was 22–23 cubic meters/minute. In order to insure satisfactory evacuation the exhaust fan was operated for 5 minutes between tests and an olfactory check was made to determine if any residual odor could be detected prior to conducting the next test.

After the test chamber had been suitably evacuated, the malodor to be utilized was sprayed from the aerosol can for about 5 seconds. After a delay of from 10–15 seconds the fragrance composition aerosol was sprayed for about 5 seconds (5 seconds being an average usage time). One minute thereafter a test panel consisting of 6 to 8 persons entered the test chamber, performed an olfactory evaluation for detection of the malodor and recorded observations. All tests were performed with only one (1) member of the panel being aware of the identity of the material being tested.

Based on flow rates through the valves utilized in the aerosol cans, the approximate amounts of aerosol containing the malodor concentrate introduced into the test chamber were 267 mg./cu.meter.

The amount of aerosol containing the fragrance compositions introduced into the test chamber was approximately 260 mg./cu.meter.

The above-described test procedure was carried out using the floral spice fragrance composition described above containing each of the compounds set forth in Examples 1 through 14, above. The results of the tests are set forth below:

| Example | Panel Ratio* |
|---------|--------------|
| 1 | 0/7 |
| 2 | 1/6 |
| 3 | 2/5 |
| 4 | ⅓ |
| 5 | 0/7 |

-continued

| Example | Panel Ratio* |
| --- | --- |
| 6 | 4/3 |
| 7 | 3/3 |
| 8 | 1/5 |
| 9 | 0/7 |
| 10 | 4/4 |
| 11 | ¾ |
| 12 | 2/6 |
| 13 | 1/7 |
| 14 | 0/8 |

*The Panel Ratio expresses the ratio of the number of panelists perceiving malodor to the number of panelists not perceiving malodor The tests results are particularly surprising because when the floral spice fragrance composition aerosol not containing the test compounds is tested at least 60 percent of the test panel detected the presence of malodor.

While the invention has been described herein with regard to certain specific embodiments, it is not so limited. It is to be understood that variations and modifications thereof may be made by those skilled in the art without departing from the spirit and scope of the invention.

The embodiments of this invention in which an exclusive property or privilege is claimed are defined as follows:

1. A fragrance composition having malodor counteractant properties comprising (i) a compound having malodor counteractant properties in an effective amount to counteract malodors and (ii) a plurality of fragrance materials in an effective amount to provide a fragrance; said compound (i) having the formula

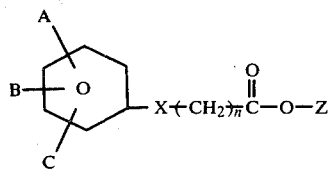

wherein
A, B and C individually represent hydrogen or an alkyl group of 1 to 6 carbon atoms provided that the total combined number of carbon atoms of A, B, C does not exceed 8 carbon atoms:
X is O;
n represents 1 to 2; and
Z represents a monohydroxy alkyl group of 2 to 7 carbon atoms.

2. Composition of claim 1 wherein, in said compound, n is 1.

3. Composition of claim 1 wherein said compound is 2-hydroxyethyl phenoxyacetate.

4. Composition of claim 1 wherein said compound is 2-hydroxyethyl p-tert-butylphenoxyacetate.

5. Composition of claim 1 wherein said compound is 6-hydroxylhexyl phenoxyacetate.

6. Composition of claim 1 wherein said compound is 4-hydroxybutyl phenoxyacetate.

7. Composition of claim 1 wherein said compound is 3-hydroxypropyl-2'-methylphenoxyacetate.

8. Composition of claim 1 wherein said compound is 3-hydroxy-1-butyl phenoxyacetate.

9. Composition of claim 1 wherein said compound is 1-hydroxy-3-butyl phenoxyacetate.

10. Composition of claim 1 wherein said compound is 3-hydroxypropyl phenoxyacetate.

11. Composition of claim 1 wherein said compound is 2-hydroxy-1-propyl phenoxyacetate.

12. Composition of claim 1 wherein said compound is 1-hydroxy-2-propyl phenoxyacetate.

13. Composition of claim 1 wherein said compound is 2-hydroxy-1-propyl-p-isopropylphenoxyacetate.

14. Composition of claim 1 wherein said compound is 1-hydroxy-2-propyl-p-isopropylphenoxyacetate.

15. Composition of claim 1 wherein said compound is 2-hydroxyethyl 3', 4'-dimethylphenoxyacetate.

16. Composition of claim 1 wherein, in said compound, n is 2.

17. Composition of claim 1 wherein said compound is 2'-hydroxyethyl 3-phenoxypropionate.

18. A composition according to claim 1 or 2 wherein A is a tert.-butyl group.

19. A composition according to claim 1 or 2 wherein C is hydrogen.

20. A composition according to claim 1 or 2 wherein B is hydrogen or methyl.

21. A composition according to claim 1 or 2 wherein Z represents a monohydroxy alkyl group of 2-4 carbon atoms.

22. A composition according to claim 20 wherein A is hydrogen or methyl, B is hydrogen or methyl, C is hydrogen, n is 1 and Z is a monohydroxy alkyl group of 2 or 3 carbon atoms.

23. A composition according to claim 20 wherein A is alkyl of 1 to 4 carbon atoms, B and C are hydrogen, n is 1 and Z is a monohydroxy alkyl group of 2-4 carbon atoms.

24. A method of treating air containing malodors to alleviate their offensive odors which comprises treating said air with an amount effective to counteract the malodor of a compound having the formula

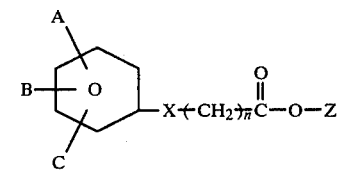

wherein
A, B and C individually represent hydrogen or an alkyl group of 1 to 6 carbon atoms provided that the total combined number of carbon atoms of A, B, C does not exceed 8 carbon atoms;
X is O
n represents 1 or 2; and
Z represents a monohydroxy alkyl group of 2 to 7 carbon atoms.

25. The method of claim 24 wherein said compound is a mixture of 2-hydroxy-1-propyl phenoxyacetate and 1-hydroxy-2-propyl phenoxyacetate.

26. The method of claim 24 wherein said compound is 2-hydroxyethyl phenoxyacetate.

27. The method of claim 24 wherein said compound is 2-hydroxy-1-propyl phenoxyacetate.

28. A fragrance composition having malodor counteractant properties comprising (i) 2-hydroxyethyl-5',6',7',8'-tetrahydronaphthoxyacetate, as a malodor counteractant, in an effective amount to counteract malodors and (ii) a plurality of fragrance materials.

29. A method of treating air containing malodors to alleviate their offensive odors which comprises treating said air with an amount effective to counteract the malodor, of the compound 2-hydroxyethyl-5',6',7',8'-tetrahydronaphthoxyacetate.

* * * * *